(12) United States Patent
Podhajsky

(10) Patent No.: US 8,333,759 B2
(45) Date of Patent: Dec. 18, 2012

(54) ENERGY DELIVERY ALGORITHM FOR MEDICAL DEVICES

(75) Inventor: Ronald J. Podhajsky, Boulder, CO (US)

(73) Assignee: Covidien LP, Mansfield, MA (US)

( * ) Notice: Subject to any disclaimer, the term of this patent is extended or adjusted under 35 U.S.C. 154(b) by 542 days.

(21) Appl. No.: 12/351,947

(22) Filed: Jan. 12, 2009

(65) Prior Publication Data

US 2010/0179533 A1 Jul. 15, 2010

(51) Int. Cl.
*A61B 18/18* (2006.01)
(52) U.S. Cl. .......................................... 606/34; 616/38
(58) Field of Classification Search ............... 606/32–52; 607/96, 98, 99, 101
See application file for complete search history.

(56) References Cited

U.S. PATENT DOCUMENTS

| | | | |
|---|---|---|---|
| 4,200,104 A | 4/1980 | Harris | |
| 5,931,836 A | 8/1999 | Hatta | |
| 5,954,719 A | 9/1999 | Chen et al. | |
| 6,080,149 A | 6/2000 | Huang et al. | |
| 6,123,702 A | 9/2000 | Swanson et al. | |
| 6,183,468 B1 | 2/2001 | Swanson et al. | |
| 6,186,147 B1 | 2/2001 | Cobb | |
| 6,231,569 B1 | 5/2001 | Bek | |
| 6,245,065 B1 | 6/2001 | Panescu et al. | |
| 6,398,779 B1 | 6/2002 | Buysse et al. | |
| 6,423,057 B1 | 7/2002 | He et al. | |
| 6,494,880 B1 | 12/2002 | Swanson et al. | |
| 6,544,260 B1 | 4/2003 | Markel et al. | |
| 6,936,047 B2 | 8/2005 | Nasab et al. | |
| 6,939,346 B2 | 9/2005 | Kannenberg et al. | |
| 6,962,587 B2 | 11/2005 | Johnson et al. | |
| 7,226,447 B2 | 6/2007 | Uchida et al. | |
| 7,258,688 B1 | 8/2007 | Shah et al. | |
| 7,303,557 B2 | 12/2007 | Wham et al. | |
| 2002/0068931 A1 | 6/2002 | Wong | |
| 2003/0171745 A1 | 9/2003 | Francischelli | |
| 2003/0199863 A1 | 10/2003 | Swanson et al. | |
| 2005/0004567 A1 | 1/2005 | Daniel | |
| 2007/0173804 A1* | 7/2007 | Wham et al. | 606/34 |
| 2007/0173806 A1 | 7/2007 | Orszulak et al. | |
| 2007/0173811 A1* | 7/2007 | Couture et al. | 606/39 |
| 2007/0282320 A1 | 12/2007 | Buysse et al. | |
| 2007/0293858 A1 | 12/2007 | Fischer | |
| 2008/0082095 A1 | 4/2008 | Shores | |
| 2008/0262489 A1 | 10/2008 | Steinke | |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |

(Continued)

OTHER PUBLICATIONS

International Search Report EP 10150566 dated Jun. 10, 2010.

(Continued)

*Primary Examiner* — Matthew F Desanto

(57) ABSTRACT

A method for controlling energy applied to tissue as a function of at least one detected tissue property includes the initial step of applying energy to tissue. The method also includes detecting a phase transition of the tissue based on a detected rate of change in the at least one detected tissue property. The method also includes adjusting the energy applied to tissue based on the detected rate of change to control the detected phase transition.

19 Claims, 4 Drawing Sheets

FOREIGN PATENT DOCUMENTS

| | | |
|---|---|---|
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1472984 | 11/2004 |
| EP | 1500378 | 1/2005 |
| EP | 880220 | 6/2006 |
| EP | 1810630 | 7/2007 |
| EP | 1862137 | 12/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 9410922 | 5/1994 |
| WO | WO03047446 | 6/2003 |
| WO | WO2008003058 | 1/2008 |
| WO | WO2008011575 | 1/2008 |
| WO | WO2008070562 | 6/2008 |
| WO | WO 2008070562 | 6/2008 |

OTHER PUBLICATIONS

International Search Report EP 10150567 dated Jun. 10, 2010.
International Search Report EP 10150563 dated Jun. 10, 2010.
International Search Report EP 10164740 dated Aug. 3, 2010.
U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.

International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
European Search Report for European Application No. 10150564.2 dated Mar. 18, 2010.

* cited by examiner

ENERGY DELIVERY ALGORITHM FOR MEDICAL DEVICES

BACKGROUND

1. Technical Field

The present disclosure relates to electrosurgical apparatuses, systems and methods. More particularly, the present disclosure is directed to an algorithm that controls the application of energy to tissue.

2. Background of Related Art

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and change thereof across the tissue at the surgical site provides a good indication of the state of desiccation or drying of the tissue, e.g., as the tissue dries or loses moisture, the impedance across the tissue rises. This observation has been utilized in some electrosurgical generators to regulate the electrosurgical power based on a measurement of tissue impedance. For example, commonly-owned U.S. Pat. No. 6,210,403 relates to a system and method for automatically measuring the tissue impedance and altering the output of the electrosurgical generator based on the measured impedance across the tissue.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform is preferred. Energy may be supplied in a continuous fashion to seal vessels in tissue if the energy input/output is responsive to tissue hydration/volume through feedback control. Delivery of the electrosurgical energy in pulses allows the tissue to cool down and also allows some moisture to return to the tissue between pulses which are both known to enhance the sealing process.

SUMMARY

According to an embodiment of the present disclosure, a method for controlling energy applied to tissue as a function of at least one detected tissue property includes the initial step of applying energy to tissue. The method also includes detecting a phase transition of the tissue based on a detected rate of change in the at least one detected tissue property. The method also includes adjusting the energy applied to tissue based on the detected rate of change to control the detected phase transition.

According to another embodiment of the present disclosure, a method for controlling energy applied to tissue as a function of at least one detected tissue property includes the initial step of applying energy to tissue. The method also includes the steps of detecting a phase transition of the tissue over a first duration of time based on a detected rate of change in the at least one detected tissue property and detecting a phase transition of the tissue over a second duration of time based on a detected rate of change in the at least one detected tissue property. The second duration of time is longer than the first duration of time. The method also includes the step of adjusting the energy applied to tissue based on the detected phase transition over at least one of the first duration of time and the longer second duration of time.

According to another embodiment of the present disclosure, a method for controlling energy applied to tissue as a function of at least one detected tissue property includes the initial step of applying energy to tissue. The method also includes the steps of initially adjusting the energy applied to tissue and determining a direction of change of the at least one detected tissue property. The method also includes the step of subsequently adjusting the energy applied to tissue in the same direction as the initially adjusting step if the at least one detected tissue property is changing in a first direction and in the opposite direction to the initially adjusting step if the at least one detected tissue property is changing in a second direction. The method also includes the step of further adjusting the energy applied to the tissue in the same direction as the initially adjusting step if the at least one detected tissue property is changing in the second direction and in the opposite direction to the initially adjusting step if the at least one detected tissue property is changing in the first direction. The method also includes the steps of detecting a phase transition of the tissue based on a detected rate of change in the at least one detected tissue property and adjusting the energy applied to tissue based on the detected rate of change to control the detected phase transition.

BRIEF DESCRIPTION OF THE DRAWINGS

Various embodiments of the present disclosure are described herein with reference to the drawings wherein.

DETAILED DESCRIPTION

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument or an open instrument.

A generator according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1:
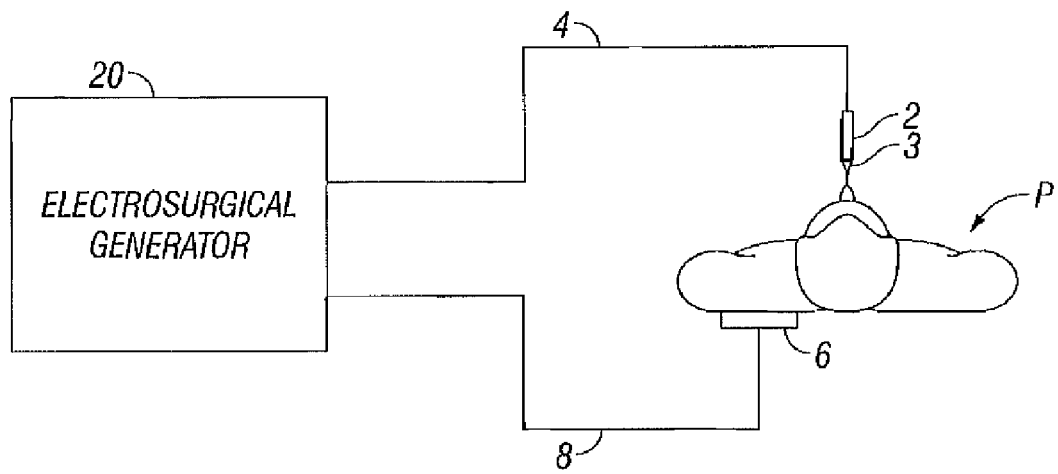
FIG. 1 is a schematic block diagram of an electrosurgical system according to the present disclosure.

FIG. 1 is a schematic illustration of a monopolar electrosurgical system according to one embodiment of the present disclosure. The system includes a monopolar electrosurgical instrument 2 including one or more active electrodes 3, which can be electrosurgical cutting probes, ablation electrode(s), etc. Electrosurgical RF energy is supplied to the instrument 2 by a generator 20 via a supply line 4, which is connected to an active terminal 30 (FIG. 2) of the generator 20, allowing the instrument 2 to coagulate, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Not explicitly shown in FIG. 1, the generator 20 includes suitable input controls (e.g., buttons, activators, switches, touch screen, etc.) for controlling the generator 20, as well as one or more display screens for providing the surgeon with a variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 2 may include a plurality of input controls which may be redundant with certain input controls of the generator 20. Placing the input controls at the instrument 2 allows for easier and faster modification of RF energy parameters during the surgical procedure without requiring interaction with the generator 20.

Figure 2:
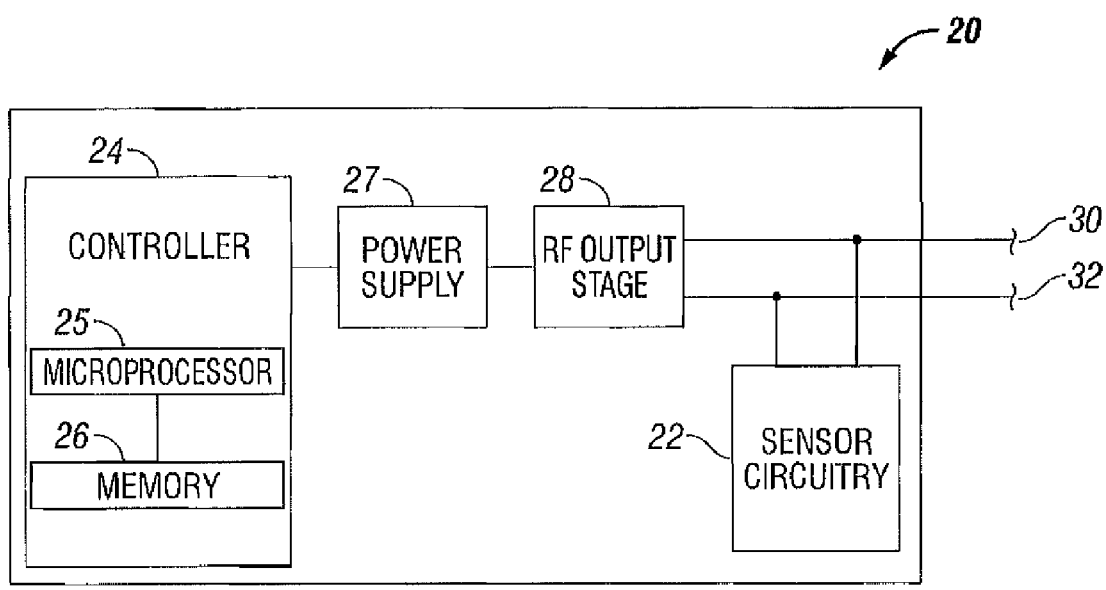
FIG. 2 is a schematic block diagram of a generator control system according to one embodiment of the present disclosure.

FIG. 2 shows a schematic block diagram of the generator 20 having a controller 24, a power supply 27, an RF output stage 28, and a sensor module 22. The power supply 27 may provide DC power to the RF output stage 28 which then converts the DC power into RF energy and delivers the RF energy to the instrument 2. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RF output stage 28 which allows the microprocessor 25 to control the output of the generator 20 according to either open and/or closed control loop schemes.

A closed loop control scheme generally includes a feedback control loop wherein the sensor module 22 provides feedback to the controller 24 (i.e., information obtained from one or more sensing mechanisms for sensing various tissue parameters such as tissue impedance, tissue temperature, output current and/or voltage, etc.). The controller 24 then signals the power supply 27 and/or RF output stage 28 which then adjusts the DC and/or RF power supply, respectively. The controller 24 also receives input signals from the input controls of the generator 20 and/or instrument 2. The controller 24 utilizes the input signals to adjust the power output of the generator 20 and/or instructs the generator 20 to perform other control functions.

The microprocessor 25 is capable of executing software instructions for processing data received by the sensor module 22, and for outputting control signals to the generator 20, accordingly. The software instructions, which are executable by the controller 24, are stored in the memory 26 of the controller 24.

The controller 24 may include analog and/or logic circuitry for processing the sensed values and determining the control signals that are sent to the generator 20, rather than, or in combination with, the microprocessor 25.

The sensor module 22 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 24. The sensor module 22 may include control circuitry which receives information from multiple sensors, and provides the information and the source of the information (e.g., the particular sensor providing the information) to the controller 24.

More particularly, the sensor module 22 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The measured or sensed values are further processed, either by circuitry and/or a processor (not explicitly shown) in the sensor module 22 and/or by the controller 24, to determine changes in sensed values and tissue impedance. Tissue impedance and changes therein may be determined by measuring the voltage and/or current across the tissue and then calculating changes thereof over time. The measured and calculated values may be then compared with known or desired voltage and current values associated with various tissue types, procedures, instruments, etc. This may be used to drive electrosurgical output to achieve desired impedance and/or change in impedance values. As the surgical procedure proceeds, tissue impedance fluctuates in response to adjustments in generator output as well as removal and restoration of liquids (e.g., steam bubbles) from the tissue at the surgical site. The controller 24 monitors the tissue impedance and changes in tissue impedance and regulates the output of the generator 20 in response thereto to achieve the desired and optimal electrosurgical effect.

In general, the system according to the present disclosure regulates the application of energy to achieve the desired tissue treatment based on properties (e.g., electrical and/or physical) of tissue. In embodiments, the application of energy to tissue is regulated based on the electrical conductivity of that tissue as a function of the tissue temperature. Tissue conductivity as a function of tissue temperature may be represented as a conductivity vs. temperature curve. Tissue conductance is inversely related to tissue impedance if the material tissue properties (e.g., length of tissue, area of tissue, etc.) remain constant. Specifically, tissue conductance and tissue impedance are related by the following equation:

$$Z=L/(\sigma*A);$$

where Z is impedance of tissue undergoing treatment;
L is the length of tissue undergoing treatment;
$\sigma$ is electrical conductance of tissue undergoing treatment; and
A is the surface area of tissue undergoing treatment.

Figure 3:
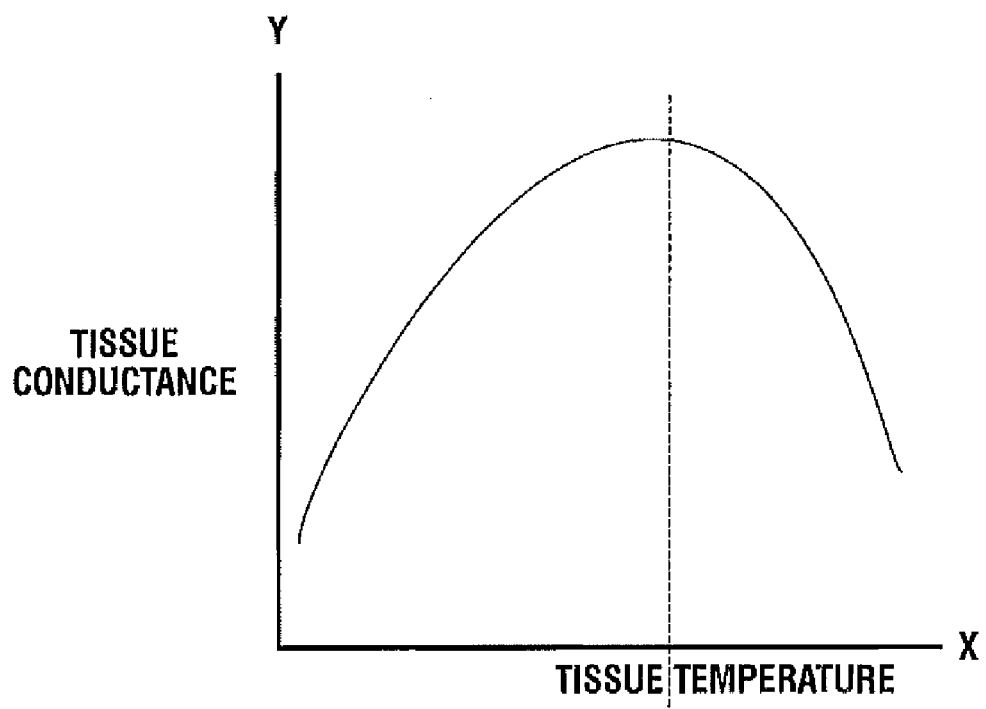
FIG. 3 illustrates a relationship between a tissue conductivity vs. temperature curve and a tissue impedance vs. temperature curve for tissue undergoing treatment.
Figure 3:
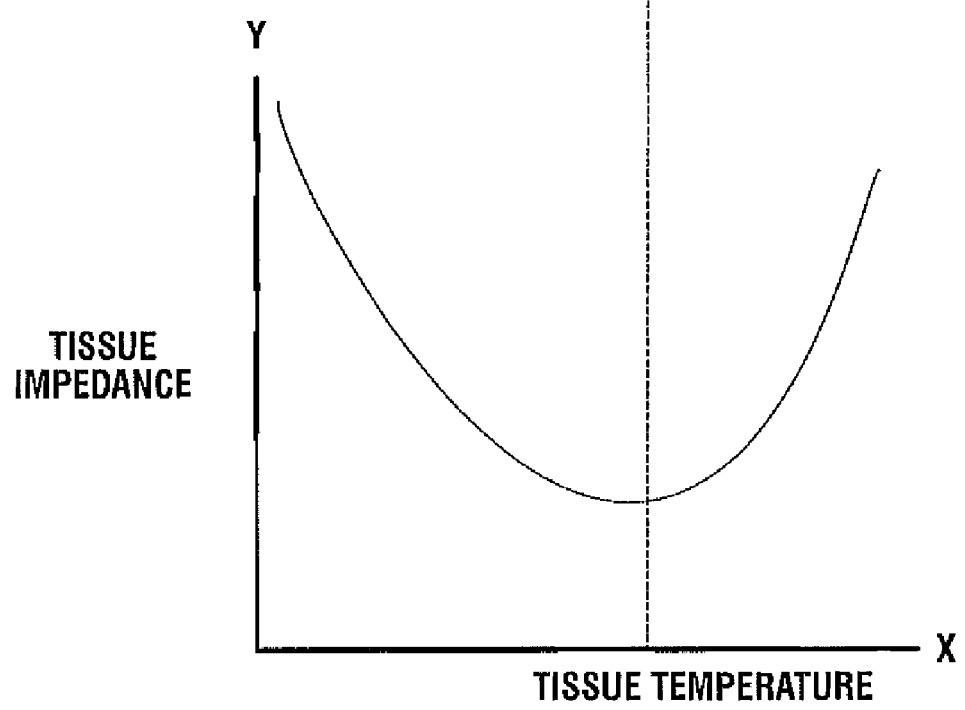

FIG. 3 illustrates the relationship between a typical conductivity vs. temperature curve and a corresponding (i.e., over the same temperature range) impedance vs. temperature curve for tissue undergoing ablation (e.g., utilizing electrosurgical instrument 2). The illustrated curves demonstrate that, for tissue undergoing ablation, the lowest impedance value on the impedance vs. temperature curve corresponds to the highest conductance value on the conductance vs. temperature curve.

The conductance vs. temperature curve for tissue undergoing ablation may be dynamically changing due a variety of factors such as, for example, the changes in energy applied to tissue. The present disclosure provides for a control algorithm that actively tracks this curve to allow for the application of energy to maintain an optimal positioning on the curve (e.g., peak tissue conductance) despite the dynamic nature of the curve.

FIG. 4 shows a flow chart illustrating a control algorithm 200 for regulating the application of energy to tissue, according to one embodiment of the present disclosure. In embodiments, algorithm 200 may be a software application residing in the memory 26 and executable by the controller 24 (e.g., via the microprocessor 25).

The control algorithm defines a state variable (SV) to express a real-time value of one or more physical properties of the tissue undergoing ablation (e.g., tissue impedance, voltage across tissue, current through tissue) and/or one or more electrical properties related to the applied energy (e.g., amplitude and/or phase of power applied to tissue, etc.). In embodiments, the SV may be defined in any one or more so-called "states". For example, the SV may represent the real-time state of tissue resistance as being either "decreasing" or "rising".

Figure 4A:
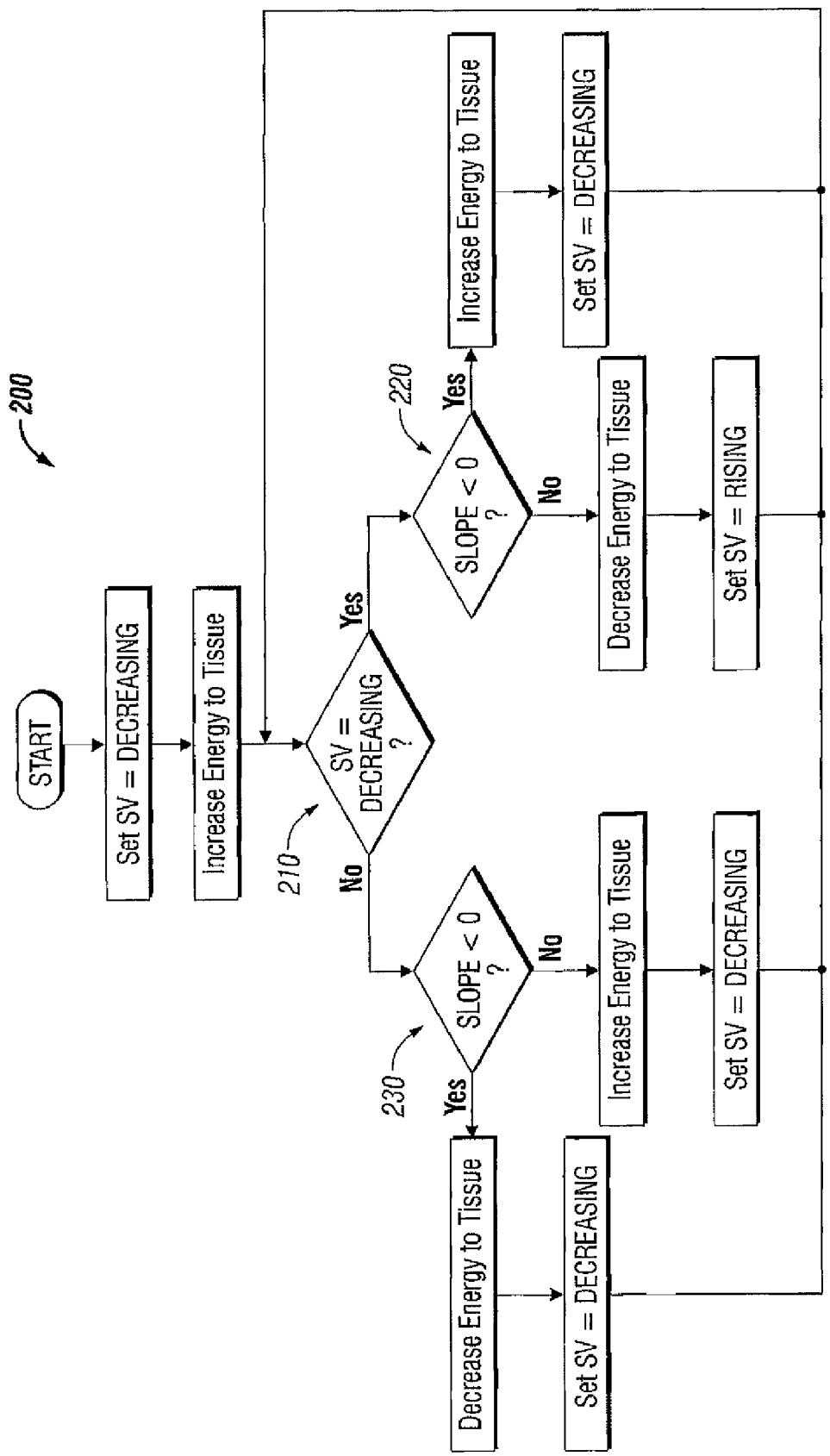
FIG. 4A is a schematic block diagram of a control algorithm according to embodiments of the present disclosure.

In the embodiment illustrated in FIG. 4A, the algorithm 200 initially defines the SV as decreasing and increases the application of energy to tissue (e.g., the controller 24 increases the output of the generator 20). Subsequently, the control algorithm 200 enters a switch loop 210 wherein the algorithm 200 continuously monitors the SV to be in any one of two states (e.g., decreasing or rising). Based on the detected state of the SV, the algorithm 200 switches between two control loops to control the application of energy to tissue.

In the illustrated embodiment, the algorithm 200 enters one of two control loops 220 and 230 to correspond to decreasing and rising states of the SV, respectively, as detected by the algorithm 200 via the switch loop 210. More specifically, the algorithm 200 enters a decreasing case control loop 220 if the switch loop 210 detects the state of the SV as decreasing. Upon entering control loop 220, the algorithm 200 continuously detects (e.g., via the sensor module 22) the slope of the control curve (e.g., the impedance vs. temperature curve of FIG. 3). If the detected slope of the control curve is negative, the algorithm 200 increases the application of energy to tissue (e.g., the controller 24 increases the output of the generator 20) and subsequently defines the SV as decreasing. In this manner, the decreasing case control loop 220 is repeated as long as the SV is defined as decreasing and the slope of the control curve is negative.

Conversely, if the detected slope of the control curve is not negative (e.g., slope=0 or slope>0), the algorithm 200 decreases the application of energy to tissue and subsequently defines the SV as rising. In this manner, the switch loop 210 detects the SV as rising and, thus, triggers the algorithm 200 to enter a rising case control loop 230.

Upon entering the rising case control loop 230, the algorithm 200 continuously detects the slope of the control curve. The rising case control loop 230 is configured such that the response to the detected slope of the control curve is directly opposite to that of the decreasing case control loop 220. More specifically, if the detected slope of the control curve is negative during the rising case control loop 230, the algorithm 200 continues to decrease the application of energy to tissue (e.g., the controller 24 further decreases the output of the generator 20) and subsequently defines the SV as decreasing. Continuing to decrease the application of energy to tissue in this scenario allows the algorithm 200 to effectively track the optimal point on the control curve (e.g., lowest possible tissue impedance as a function of temperature). Conversely, if the detected slope of the control curve is not negative (e.g., slope=0 or slope>0), the algorithm 200 increases the application of energy to tissue and subsequently defines the SV as decreasing. Increasing the application of energy to tissue in this scenario allows the algorithm 200 to effectively deliver the maximum energy to tissue. In either scenario (i.e., slope<0; and slope>0) of the rising case control loop 230, the SV is reset to decreasing such that the algorithm 200 enters or re-enters the decreasing case control loop 220. In this way, the algorithm 200 aggressively applies energy to tissue to achieve maximal tissue heating while tracking the optimal point on the control curve (e.g., the lowest possible tissue impedance).

In embodiments wherein a tissue impedance vs. temperature curve (e.g., FIG. 3) is utilized as the control curve, the decreasing case control loop 220 recognizes that a slope detected as negative corresponds to the tissue impedance as decreasing and, thus, the algorithm 200 increases the application of energy to tissue accordingly and re-enters the decreasing case control loop 220. Conversely, the decreasing case control loop 220 recognizes that a slope detected as not negative corresponds to the tissue impedance as rising and, thus, the algorithm 200 decreases the application of energy to tissue accordingly and enters the rising case control loop 230. The rising case control loop 230 recognizes that a slope detected as negative corresponds to the tissue impedance as decreasing and, thus, the algorithm 200 further decreases the application of energy to tissue to ensure the algorithm 200 finds the lowest possible tissue impedance. Conversely, the rising case control loop 230 recognizes that a slope detected as not negative corresponds to the tissue impedance as not changing or continuing to rise and, thus, the algorithm 200 increases the application of energy to tissue to ensure that the maximum energy is delivered to tissue.

Figure 4B:
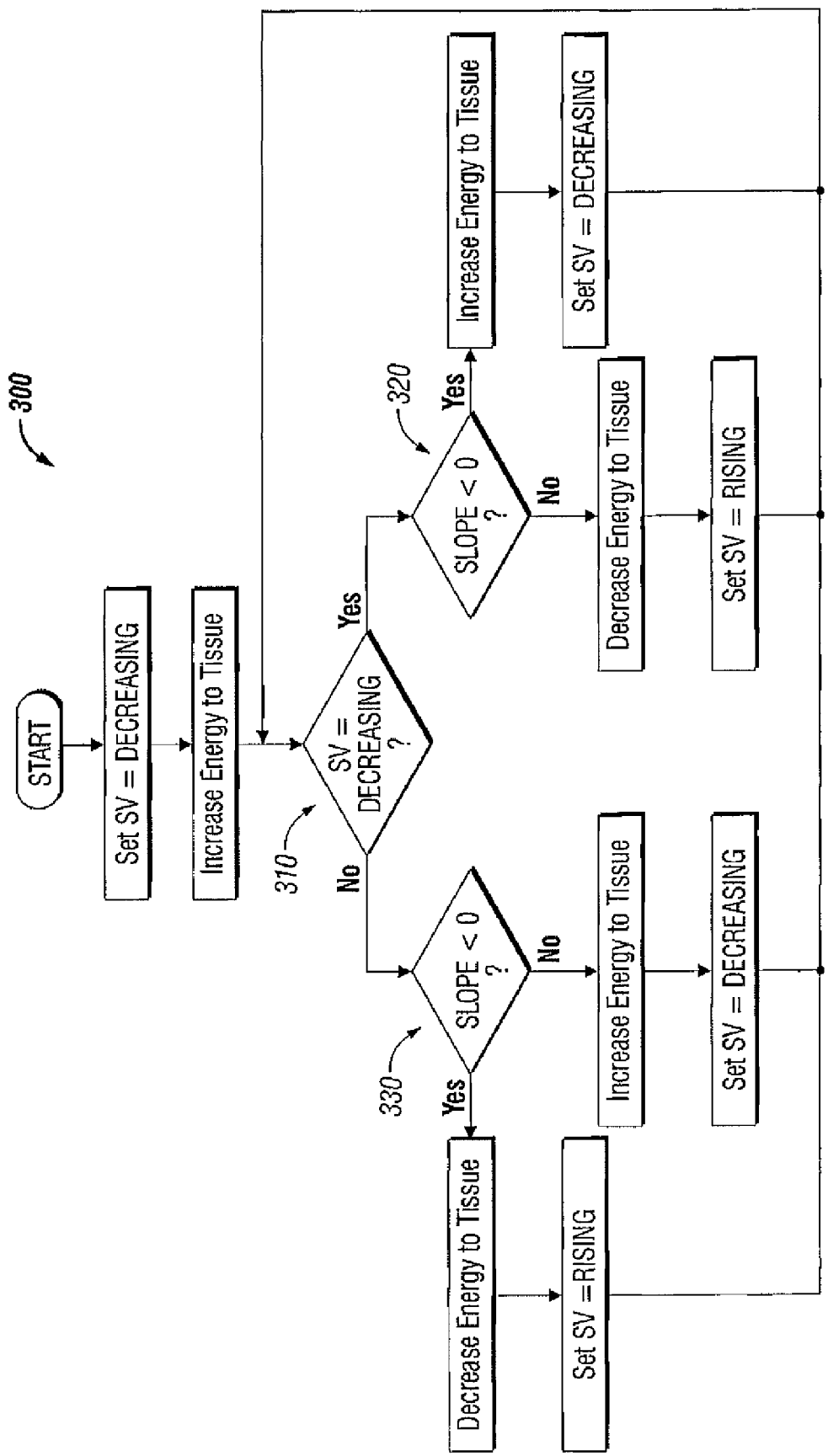
FIG. 4B is a schematic block diagram of a control algorithm according to an embodiment of the present disclosure.

In embodiments, in the case of the SV being defined as rising, if the slope of the control curve is negative, energy applied to tissue is decreased and the SV is reset to rising rather than decreasing, as is the case in the embodiment illustrated in FIG. 4A. FIG. 4B shows a flow chart illustrating an alternative algorithm 300 according to embodiments of the present disclosure. The algorithm 300 operates similarly to the algorithm 200 illustrated in FIG. 4A and is only described to the extent necessary to illustrate the differences between the embodiments. The algorithm 300 utilizes the identical initialization as that of the algorithm 200 illustrated in FIG. 4A. Further, the algorithm 300 includes a switch loop 310 configured to switch between two control loops, namely, a decreasing case control loop 320 and a rising case control loop 330 corresponding to the SV being defined as decreasing and rising, respectively.

As illustrated in FIGS. 4A and 4B, the difference between the algorithms 200 and 300 lies in the respective rising case control loops 230 and 330. In the case of the SV being defined as rising in the switch loop 310 of the algorithm 300, if the slope of the control curve is negative, the algorithm 300 decreases the energy applied to tissue and maintains the SV as rising rather than reset to decreasing, as is the case in the algorithm 200 embodied in FIG. 4A. In this manner, the rising case control loop 330 will continue to loop until the slope of the control curve is not negative (e.g., slope=0 or slope>0). In embodiments wherein a tissue impedance vs. temperature curve (e.g., FIG. 3) is utilized as the control curve, if the tissue impedance is decreasing (e.g., slope of the control curve<0), the rising case control loop 330 will continue until the algorithm 300 detects that the tissue impedance is not negative (i.e., slope of the control curve>0). Upon detection that the tissue impedance is not negative, the algorithm 300 increases the application of energy to tissue and resets the SV to decreasing.

In embodiments, one or more high priority control loops may be layered over the algorithms 200 and 300 to run concurrently therewith. The high priority control loops are configured to detect varying rates (e.g., rapid, slow, etc.) of change in tissue properties (e.g., tissue impedance, tissue temperature, etc.) and alter generator output in response thereto. During the ablation of tissue, conditions may exist that lead to continued energy increases. Such energy increases may cause tissue properties (e.g., tissue impedance, tissue temperature, etc.) to rise and/or fall outside of the peak conductance range or into a so-called "runaway state." The high priority control loop monitors the control curve for the runaway state and adjusts the application of energy (e.g., the controller 24 decreases the output of the generator 20) accordingly. More specifically, the high priority loop interrupts the algorithm (e.g., algorithm 200 and 300) to detect the rate of change of tissue properties (e.g., rapid increases in tissue impedance) that are indicative of the runaway state, and decreases the application of energy in the event that such a state is detected.

In embodiments wherein an impedance vs. temperature curve (FIG. 3) is utilized as the control curve, the high priority loop continually interrogates whether tissue impedance is rising more than a pre-determined threshold value. The pre-determined threshold value may be pre-determined by the surgeon via the generator 20 input controls and/or reside in the memory 26 for execution by the microprocessor 25. In this manner, the high priority control loop is configured to respond to rapid changes in tissue properties via alterations of generator output.

In another embodiment, a second high priority control loop runs concurrently with the high priority control loop discussed above and is configured to periodically interrupt the algorithm (e.g., algorithm 200 and 300) to check for phase transition states of tissue being treated based on a rate of change of tissue properties (e.g., rapid or slow changes in tissue impedance). In the event that such a state is detected, the second high priority control loop regulates the application of energy to tissue by increasing or decreasing generator output. More specifically, the second high priority control loop monitors the rate of change of tissue properties (e.g., tissue impedance, tissue temperature, etc.) to detect an increasing presence of phase transition in the proximity of the energy applicator (e.g., instrument 2). Phase transition of tissue being treated is the vaporization of liquids in the tissue to gas. The vaporization of the liquids in the tissue to gas is manifest as steam bubbles or a bubble field proximate the energy applicator and/or tissue site. The bubble field adversely affects the efficiency of energy application to tissue due to a resulting rise in impedance of the tissue being treated (e.g., proximate the energy applicator 2). As a field of steam bubbles form around the energy applicator, the impedance of the tissue being treated rises relatively slowly and, thus, may be easily detected and/or monitored by the second high priority control loop. In this scenario, tissue properties (e.g., tissue impedance, tissue temperature, etc.) may be monitored and/or sampled over a longer duration of time relative to the high priority control loop previously discussed hereinabove. Upon detection of a threshold rate of change in tissue properties, the generator output is altered accordingly (e.g., decreased or increased) to cause the bubble field to collapse. In this scenario, the resulting bubble field collapse causes tissue impedance to decrease. Thus, since tissue conductance is inversely proportional to tissue impedance (see FIG. 3), energy is delivered more efficiently duration of the procedure time.

The altering of generator output may range between a relatively slight decrease in generator output to a complete termination of generator output. Generator output may also be rapidly increased to momentarily cause a so-called "shock" to the bubble field via the energy applicator, which, in turn, causes the bubble field to collapse. In use, the previously discussed high priority control loop and the second high priority control loop run concurrently with the algorithm (e.g., algorithm 200 and 300) and with each other, such that the algorithm is configured to respond both rapidly and relatively slower, respectively, to changes in tissue impedance.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling energy applied to tissue as a function of at least one detected tissue property, comprising the steps of:

applying energy to tissue;

sensing an electrical conductance of the tissue;

detecting at least one bubble field proximate to tissue; and controlling the energy applied to tissue in accordance with a detected slope of a control curve to collapse the detected at least one bubble field, the control curve representative of the sensed electrical conductance of tissue as a function of tissue temperature, the controlling step including:

initially adjusting the energy applied to tissue and determining a direction of the change of the detected slope of the control curve;

subsequently adjusting the energy applied to tissue in the same direction as the initially adjusting step if the detected slope of the control curve is changing in a first direction and in the opposite direction to the initially adjusting step if the detected slope of the control curve is changing in a second direction; and further adjusting the energy applied to the tissue in the same direction as the initially adjusting step if the detected slope of the control curve is changing in the second direction and in the opposite direction to the initially adjusting step if the detected slope of the control curve is changing in the first direction.

2. A method according to claim 1, further comprising the steps of:
detecting the at least one bubble field over a first duration of time;
detecting the at least one bubble field over a second duration of time; and
adjusting the energy applied to tissue based on the detected at least one bubble field over at least one of the first duration of time and the second duration of time.

3. A method according to claim 2, wherein the second duration of time is longer than the first duration of time.

4. A method according to claim 2, further comprising:
detecting a rate of change of the electrical conductance over the first duration of time and adjusting the energy applied to tissue if the detected rate of change exceeds a pre-determined value; and
detecting a second rate of change of the electrical conductance of tissue over the second duration of time and adjusting the energy applied to tissue based on the detected rate of change to collapse the detected at least one bubble field.

5. A method according to claim 1, further comprising the steps of:
detecting the at least one bubble field continuously over a first duration of time;
detecting the at least one bubble field periodically over the second duration of time; and
adjusting the energy applied to tissue based on the at least one bubble field detected over at least one of the first duration of time and the second duration of time.

6. A method according to claim 1, wherein after the initial sensing step, the method further includes the step of sensing tissue temperature.

7. A method according to claim 1, wherein the controlling step further comprises the step of:
decreasing the energy applied to tissue to control the detected at least one bubble field.

8. A method according to claim 1, wherein after the initial sensing step, the method further includes the step of sensing tissue temperature.

9. A method for controlling energy applied to tissue as a function of at least one detected tissue property, comprising the steps of:
applying energy to tissue;
sensing an electrical conductance of tissue;
detecting at least one bubble field proximate to tissue over a first duration of time;
detecting at least one bubble field proximate to tissue over a second duration of time, the second duration of time being longer than the first duration of time; and
controlling the energy applied to tissue in accordance with a detected slope of a control curve over at least one of the first duration of time and the longer second duration of time to collapse the detected at least one bubble field, the control curve representative of the sensed electrical conductance of tissue as a function of tissue temperature, the controlling step including:
initially adjusting the energy applied to tissue and determining a direction of the change of the detected slope of the control curve;
subsequently adjusting the energy applied to tissue in the same direction as the initially adjusting step if the detected slope of the control curve is changing in a first direction and in the opposite direction to the initially adjusting step if the detected slope of the control curve is changing in a second direction; and
further adjusting the energy applied to the tissue in the same direction as the initially adjusting step if the detected slope of the control curve is changing in the second direction and in the opposite direction to the initially adjusting step if the detected slope of the control curve is changing in the first direction.

10. A method according to claim 9, further comprising:
detecting a rate of change of the sensed electrical conductance over the first duration of time and adjusting the energy applied to tissue if the detected rate of change exceeds a predetermined value; and
detecting a second rate of change of the sensed electrical conductance of tissue over the second duration of time and adjusting the energy applied to tissue based on the detected rate of change to collapse the detected least one bubble field.

11. A method according to claim 9, further comprising the steps of:
detecting the at least one bubble field continuously over a first duration of time;
detecting the at least one bubble field periodically over the second duration of time; and
adjusting the energy applied to tissue based on the at least one bubble field detected over at least one of the first duration of time and the second duration of time.

12. A method for controlling energy applied to tissue as a function of at least one detected tissue property, comprising the steps of:
applying energy to tissue;
sensing an electrical conductance of tissue; and
controlling the energy applied to tissue in accordance with a detected slope of a control curve, the control curve representative of the sensed electrical conductance of tissue as a function of tissue temperature, the controlling step including:
initially adjusting the energy applied to tissue and determining a direction of change of the at least one detected tissue property;
subsequently adjusting the energy applied to tissue in the same direction as the initially adjusting step if the detected slope of the control curve is changing in a first direction and in the opposite direction to the initially adjusting step if the detected slope of the control curve is changing in a second direction;
further adjusting the energy applied to the tissue in the same direction as the initially adjusting step if the detected slope of the control curve is changing in the second direction and in the opposite direction to the initially adjusting step if the detected slope of the control curve is changing in the first direction;
detecting at least one bubble field proximate to tissue based on the detected slope of the control curve; and
adjusting the energy applied to tissue based on the detected slope of the control curve to collapse the detected at least one bubble field.

13. A method according to claim 12, further comprising the step of detecting at least one of tissue conductance and tissue temperature.

14. A method according to claim 13, further including the step of deriving a control curve based on the detected tissue conductance as a function of the detected tissue temperature.

15. A method according to claim 14, further including the step of detecting a rate of change of the control curve and adjusting the energy applied to tissue if the detected rate of change exceeds a pre-determined value.

16. A method according the claim 14, wherein the initially adjusting step further includes the step of determining a slope of the control curve to indicate the direction of change of the control curve.

17. A method according to claim 13, further comprising the step of deriving a tissue impedance based on the detected tissue conductance to derive a control curve based on the tissue impedance as a function of the tissue temperature.

18. A method according to claim 12, wherein the further adjusting step is repeated if the at least one detected tissue property is changing in the first direction.

19. A method according to claim 12, further comprising the step of repeating the subsequently adjusting step if the at least one detected tissue property is changing in the first direction.

* * * * *